(12) United States Patent
Pazenok et al.

(10) Patent No.: US 8,242,313 B2
(45) Date of Patent: Aug. 14, 2012

(54) ALKOXY ENONES AND ENAMINO KETONES AND A PROCESS FOR PREPARATION THEREOF

(75) Inventors: Sergii Pazenok, Solingen (DE); Norbert Lui, Odenthal (DE); Arnd Neeff, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 71 days.

(21) Appl. No.: 13/010,863

(22) Filed: Jan. 21, 2011

(65) Prior Publication Data

US 2012/0022285 A1   Jan. 26, 2012

Related U.S. Application Data

(63) Continuation-in-part of application No. 12/842,249, filed on Jul. 23, 2010.

(30) Foreign Application Priority Data

Jul. 23, 2009   (EP) .................... 09166239

(51) Int. Cl.
*C07C 45/00* (2006.01)
*C07C 49/00* (2006.01)
*C07D 401/00* (2006.01)
*C07C 69/66* (2006.01)

(52) U.S. Cl. ............... 568/383; 568/415; 546/275.4; 560/174; 560/262

(58) Field of Classification Search .......... 568/383, 568/415; 560/174, 262; 546/275.4
See application file for complete search history.

(56) References Cited

U.S. PATENT DOCUMENTS

| 2009/0275471 A1 | 11/2009 | Funke et al. |
| 2010/0029478 A1 | 2/2010 | Alig et al. |
| 2011/0015405 A1 | 1/2011 | Antons et al. |
| 2011/0021782 A1 | 1/2011 | Pazenok et al. |
| 2011/0028729 A1 | 2/2011 | Pazenok et al. |

FOREIGN PATENT DOCUMENTS

DE   10 2006 032 168 A1   12/2007

OTHER PUBLICATIONS

Tarasenko, K.V., et al., "Reactions of β-aminovinyl bromodifluoromethyl ketones with alkyl phosphites: Perkow versus Arbuzov," *Collect. Czech. Chem. Commun.* 74:335-346, Institute of Organic Chemistry and Biochemistry, Czech Republic (2009).

Martins, M.A.P., et al., "A convenient synthesis of 5-trichloromethyl-5-hydroxy-3-heteroalkyl-4,5-dihydroisoxazoles," *Synthesis* 13:1959-1964, Thieme Publishing Group, Germany (2001).

*Primary Examiner* — Sikarl Witherspoon
(74) *Attorney, Agent, or Firm* — Sterne, Kessler, Goldstein & Fox P.L.L.C.

(57) ABSTRACT

The present invention relates to novel alkoxy enones and enamino ketones, and to a novel process for preparation thereof. Alkoxy enones and enamino ketones are valuable intermediates for preparation of pyrazoles and anthranilamides, which can be used as insecticides.

10 Claims, No Drawings

ALKOXY ENONES AND ENAMINO KETONES AND A PROCESS FOR PREPARATION THEREOF

This application is a continuation-in-part of application Ser. No. 12/842,249, filed Jul. 23, 2010, now pending. The patent application identified above is incorporated here by reference in its entirety to provide continuity of disclosure.

The present invention relates to novel alkoxy enones and enamino ketones, and to a novel process for preparation thereof. Alkoxy enones and enamino ketones are valuable intermediates for preparation of pyrazoles and anthranilamides, which can be used as insecticides.

The literature discloses that 5-bromo-1,1,1-trihalo-4-methoxypent-3-en-2-one has three reaction sites (on the carbonyl carbon and on the C4 and C5 carbons) which can react in different ways according to the type of nucleophile and conditions. For instance, Gems et al. (Coll. Czech Chem. Comm, 2009, v. 74, N 2, p. 335-346) states that alkoxy ketones react with triethyl phosphites to form "Arbuzov" products of the formula (IX) or "Perkov" products of the formula (X) (see following scheme (A)):

Scheme (A)

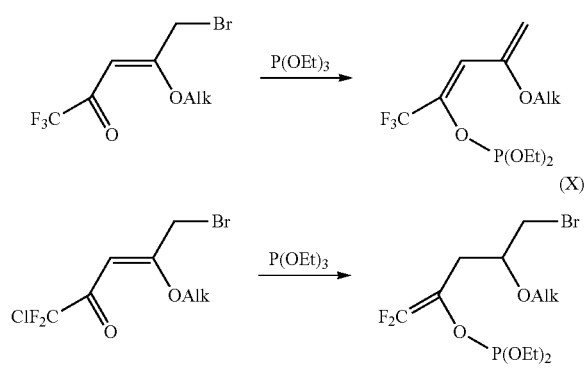

It is an object of the invention to provide a process which allows the halogen atom in position 5, for example of the 5-halo-1,1,1-trihalo-4-(alkoxy)pent-3-en-2-one or 5-halo-1,1,1-trihalo-4-(dialkyl-amino)pent-3-en-2-one compounds, to be exchanged selectively for O-nucleophiles without attacking the trihalomethyl group on the carbonyl carbon. The process should be suitable for the industrial production of the product. It is a further object of the present invention to develop a process which allows alkoxy enones and enamino ketones to be provided in a sufficient amount and purity for the further preparation of pyrazoles and anthranilamides.

The object was achieved in accordance with the invention by a process for preparing the alkoxy enones and enamino ketones of the formula (I)

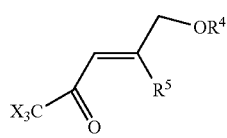

(I)

in which $R^4$ is hydrogen, —(C=O)alkyl, (C=O)haloalkyl, —(C=O)O-alkyl, $SO_2$alkyl, $SO_2$-haloalkyl, $SO_2$-aryl, X is halogen, $R^5$ is alkoxy, dialkylamino where the alkyl groups may optionally form a ring which may optionally contain 1-2 further heteroatoms from the group of O, N, S, or is cycloalkylamino, thioalkyl, characterized in that the compounds of the general formula (III)

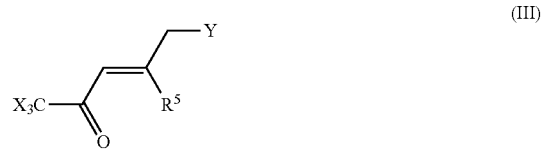

(III)

in which $R^5$ and X are as defined above and Y is independently fluorine, chlorine, bromine or iodine are reacted with a compound of the general formula (II)

$$KatOR^4 \quad (II)$$

in which

Kat is a cation, and is Li, Na, K, Cs, $(alkyl)_4N$, $(alkyl)_4P$, $(aryl)_4P$, $R^4$ is hydrogen, —(C=O)alkyl, (C=O)haloalkyl, —(C=O)O-alkyl, $SO_2$alkyl, $SO_2$-haloalkyl, $SO_2$-aryl, $R^4$ is preferably —(C=O)($C_1$-$C_6$)alkyl, (C=O)halo($C_1$-$C_6$)alkyl, —(C=O)O—($C_1$-$C_6$)alkyl, $SO_2$($C_1$-$C_6$)alkyl, $SO_2$-halo($C_1$-$C_6$)alkyl, $SO_2$-aryl, $R^4$ is more preferably —(C=O)($C_1$-$C_6$)alkyl, $R^4$ is most preferably —(C=O)$CH_3$, to give inventive alkoxy enones and enamino ketones of the formula (I), which can be processed further to give pyrazoles and anthranilamides.

The process affords the inventive compounds of the formula (I) with no side reactions and thus does not have the disadvantages described in the prior art.

More particularly, it is considered to be completely surprising that 5-halo-1,1,1-trihalo-4-alkoxy- or -(dialkylamino)pent-3-en-2-one reacts regioselectively with the compounds of the formula (II) and exchanges the halogen atom in position 5 for O-nucleophiles, for example the $OR^4$ group, without attacking the trihalomethyl group $X_3CO$—.

Scheme (B)

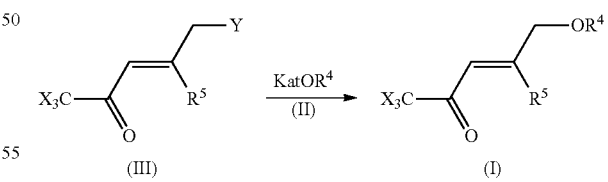

where Kat, X, Y, $R^4$, $R^5$ are each as defined above.

GENERAL DEFINITIONS

In the context of the present invention, the term "halogens (independently X or Y)", unless defined otherwise, encompasses those elements which are selected from the group consisting of fluorine, chlorine, bromine and iodine, preference being given to using fluorine, chlorine and bromine and particular preference to using fluorine and chlorine. Substituted groups may be mono- or polysubstituted, and the substituents in the case of polysubstitutions may be the same or different.

Alkyl groups substituted by one or more halogen atoms (—X) (=haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

In the context of the present invention, unless defined differently, alkyl groups are linear or branched hydrocarbon groups.

The definition "alkyl" and "$C_1$-$C_{12}$-alkyl" encompasses, for example, the meanings of methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, cycloalkyl groups, unless defined differently, are cyclic saturated hydrocarbon groups which may optionally contain 1-3 heteroatoms from the group of O, N, S.

In the context of the present invention, aryl radicals, unless defined differently, are $C_6$-$C_{10}$ aromatic hydrocarbon radicals and aromatic hydrocarbon radicals which may have one, two or more heteroatoms selected from O, N, P and S, and may optionally be substituted by further groups.

The inventive compounds may optionally be present as mixtures of different possible isomeric forms, especially of stereoisomers, for example E and Z, threo and erythro, and optical isomers, but if appropriate also of tautomers. Both the E and Z isomers, and also the threo and erythro isomers, and also the optical isomers, any desired mixtures of these isomers, and the possible tautomeric forms, are disclosed and claimed.

Compounds of the Formula (III)

The compounds used as starting materials in the performance of the process according to the invention are defined in general terms by the formula (III):

$$X_3C-\underset{O}{\overset{}{C}}-CH=C(R^5)-CH_2-Y \quad (III)$$

where

X is independently fluorine, chlorine, bromine, iodine, preferably fluorine, chlorine or bromine, more preferably chlorine or bromine, Y is independently fluorine, chlorine, bromine or iodine, $R^5$ is alkoxy, dialkylamino where the alkyl groups may optionally form a ring which may optionally contain 1-2 further heteroatoms from the group of O, N, S, or is cycloalkylamino, thioalkyl, preferably alkoxy, more preferably ($C_1$-$C_6$)alkoxy.

5-Halo-1,1,1-trihalo-4-methoxypent-3-en-2-ones can be prepared by the method of Gerus et al., Synthesis 2001, 3, 431-436.

Examples of compounds of the formula (III) suitable in accordance with the invention are, for example:

5-bromo-1,1,1-trichloro-4-methoxypent-3-en-2-one,
5-chloro-1,1,1-trichloro-4-methoxypent-3-en-2-one,
5-bromo-1,1,1-trifluoro-4-methoxypent-3-en-2-one,
5-bromo-1,1,1-trichloro-4-ethoxypent-3-en-2-one, 5-chloro-1,1,1-trifluoro-4-methoxypent-3-en-2-one, 5-chloro-1,1,1-trifluoro-4-dimethylamino-pent-3-en-2-one.

Compounds of the Formula (II)

The compounds used as starting materials in the course of performance of the process according to the invention are defined in general terms by the formula (II)

$$KatOR^4 \quad (II),$$

where Kat and $R^4$ are each as defined above.

The following compounds of the formula (II) are listed in an illustrative but nonlimiting manner: NaOAc, KOAc, CsOAc, $CF_3COONa$, $CF_3COOK$, $CCl_3COONa$, $CH_3SO_3Na$, $PhenylSO_3Na$, $Bu_4NOCOCH_3$.

The compounds of the formula (II) are commercially available.

The inventive process step is preferably performed within a temperature range from 10° C. to 100° C., more preferably at temperatures of 20° C. to 80° C. The inventive process step is generally performed under standard pressure.

The reaction time is not critical and may, depending on the batch size and temperature, be selected within a range between 30 min and several hours.

In the performance of the inventive process step, 1 mol of the halo enone of the formula (III) is reacted with 0.8 to 2.0 mol; or 0.8 mol to 1.5 mol, preferably 0.9 mol to 1.2 mol, more preferably with an equimolar amount, of the compound of the formula (II).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alcohols such as methanol, ethanol, isopropanol. Particular preference is given to using acetonitrile, toluene, ethanol, THF, diglyme, N-methylpyrrolidone, 1,2-diethoxyethane.

The reaction can be accelerated by the addition of catalysts.

The catalysts used may be substances which generally accelerate reactions with O-nucleophiles. For example, it is possible to use alkali metal bromides or alkali metal iodides, for example sodium iodide, potassium iodide, potassium bromide, ammonium bromide or ammonium iodide; tetraalkylammonium iodides, tetraalkylammonium bromides or tetraalkylammonium sulphates, for example tetraethylammonium chloride, tetraethylammonium bromide, tetrabutylammonium chloride or tetrabutylammonium bromide; tetraalkyl- or tetraarylphosphonium chlorides or bromides or iodides, for example bis(dimethylamino)[(1,3-dimethylimidazolidin-2-ylidene)amino]methylium bromide, hexadecyltributylphosphonium bromide, stearyltributylphosphonium bromide, tetrabutyl-phosphonium bromide, tetrabutylphosphonium bromide, tetraoctylphosphonium bromide, tetraphenylphosphonium chloride, tetraphenylphosphonium bromide, tetrakis(dimethyl-amino)phosphonium bromide, tetrakis(diethylamino)phosphonium bromide, tetrakis(dipropyl-amino)phosphonium chloride or bromide; crown ethers, for example 18-crown-6.

The amount of the catalyst may be varied from 0.1 to 15 percent by weight, based on the compound of the formula (II) used. Higher amounts of catalyst are possible but uneconomic.

Martins et al. (Synthesis 2001, 13, 1959) states that 5-bromo-1,1,1-trichloro-4-methoxypent-3-en-2-one reacts with phenol in the presence of potash at 80° C. in acetonitrile with Br/OPh exchange.

In the present case, this reaction gave rise to a complex mixture of several products, and the degradation of the $CCl_3$ group was dominant.

In order to prevent the halo form degradation (particularly in the case of $CCl_3$ enones), the acid is added to the reaction mixture, which lowers the basicity of the reaction mixture. This significantly suppresses the formation of by-products as a result of degradation of the $CCl_3$ group. The amount of the acid may be varied from 0.05 to 3 equivalents, or from 0.05 to 2 equivalents, or from 0.05 to 1 equivalent based on the compound of the formula (III) used. Useful additives include HCl, $H_2SO_4$, $CH_3COOH$, $CF_3COOH$, preference being given to $CH_3COOH$, HCl and $H_2SO_4$.

The reaction mixture is worked up anhydrously by freeing the mixture of salts (filtration) and removing the solvents under reduced pressure. Aqueous workup is also possible. It is also possible to further convert the mixture without intermediate isolation.

The purity of the compounds of the formula (I) is very high and is in the range of 95-97%, which allows the compounds to be used further without a purification step. More particularly, the inventive reaction is notable for the use of inexpensive raw materials, and for a process regime which can be performed particularly efficiently and simply even on the industrial scale.

The inventive compounds of the formula (I) are important intermediates for the preparation of pyrazoles according to Scheme (C), which in turn are valuable intermediates in the synthesis of anthranilamides (WO2007/112893, WO2007/144100).

Scheme (C)

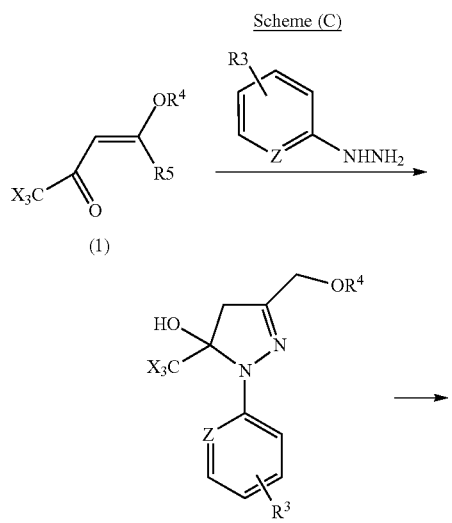

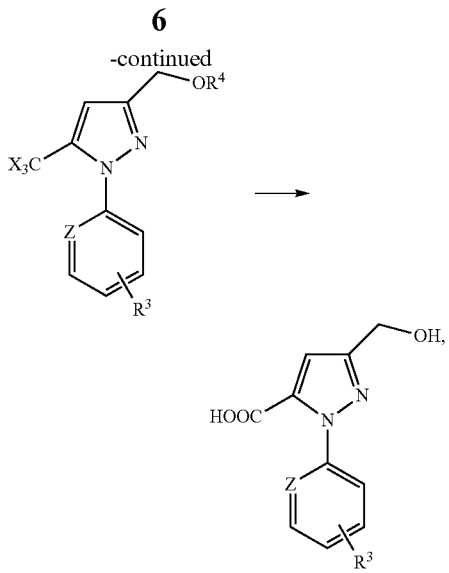

where
Z is CH, N,
$R^3$ is H, halogen, CN, $NO_2$, alkyl, cycloalkyl, haloalkyl, halocycloalkyl, alkoxy, haloalkoxy, alkylamino, dialkylamino, cycloalkylamino and
$R^4$, $R^5$ and X are each as defined above.

PREPARATION EXAMPLES

Example 1

5-Bromo-1,1,1-trichloro-4-methoxypent-3-en-2-one was prepared by the method of Gerus et. al., Synthesis 2001, 3, 431-436, yield 90%.

Example 2

5,5,5-Trichloro-2-methoxy-4-oxopent-2-en-1-yl acetate 29.6 g (0.1 mol) of 5-bromo-1,1,1-trichloro-4-methoxypent-3-en-2-one, 17 g of potassium acetate, 5 g of tetrabutylammonium bromide and 8 g of acetic acid were stirred in 300 ml of acetonitrile at 40° C. for 16 h. The mixture was concentrated under reduced pressure, and water was added to the residue. The product was extracted with ethyl acetate, the organic phase was washed with water and the solvent was removed fully under reduced pressure.

This gave 25.4 g (85%) of the product as a light brown solid with the LC purity of 97%, m.p. 53-55° C.
$^1$H NMR (DMSO $d_6$) δ: 2.05 (s, 3H), 3.85 (s, 3H), 5.2 (s, 2H), 6.1 (s, 1H) ppm.
GC/MS: m/z 274.

Example 3

5,5,5-Trichloro-2-methoxy-4-oxopent-2-en-1-yl acetate 29.6 g (0.1 mol) of 5-bromo-1,1,1-trichloro-4-methoxypent-3-en-2-one, 19.1 g of cesium acetate, 5 g of tetrabutylammonium bromide and 8 g of acetic acid were stirred in 300 ml of acetonitrile at 25° C. for 8 h. The precipitate was filtered off and the organic phase was concentrated under reduced pressure.

This gave 26.8 g (90%) of the product as a light brown solid with the LC purity of 98%, m.p. 54-55° C.

Example 4

5,5,5-Trifluoro-2-methoxy-4-oxopent-2-en-1-yl acetate 24.8 g (0.1 mol) of 5-bromo-1,1,1-trifluoro-4-methoxy-pent-3-en-2-one, 20 g of potassium acetate, 5 g of tetrabutylammonium bromide and 8 g of acetic acid were stirred in 300 ml of acetonitrile at 40° C. for 20 h. The precipitate was filtered off and the solvent was removed completely under reduced pressure.

This gave 15.8 g (70%) as a light brown oil with a purity of 85%.

$^1$H NMR (DMSO $d_6$) δ: 2.17 (s, 3H), 3.80 (s, 3H), 5.28 (s, 2H), 6.15 (s, 1H) ppm. GC/MS: m/z 226.

Example 4b

[1-(3-Chloropyridin-2-yl)-5-(trichloromethyl)-1H-pyrazol-3-yl]methyl acetate 38.7 g of [1-(3-chloropyridin-2-yl)-5-hydroxy-5-(trichloromethyl)-4,5-dihydro-1H-pyrazol-3-yl]-methyl acetate were dissolved in 200 ml of methyl tert-butyl ether, and 12.6 g of oxalyl chloride were added dropwise within 2 h (vigorous evolution of gas). The mixture was stirred at 25° C. for a further 5 h and concentrated completely under reduced pressure.

This gave 36 g of the product as a viscous oil which crystallized through after approx. 10 h at room temperature, m.p. 40-42° C.

$^1$H NMR (DMSO $d_6$) δ: 2.0 (s, 3H), 5.1 (dd, 2H), 7.0 (s, 1H), 7.6 (dd, 1H), 8.1 (dd, 1H), 8.5 (dd, 1H) ppm.

Example 5

[1-(3-Chloropyridin-2-yl)-5-hydroxy-5-(trichloromethyl)-4,5-dihydro-1H-pyrazol-3-yl]methyl acetate 27.5 g (0.1 mol) of 5,5,5-trichloro-2-methoxy-4-oxopent-2-en-1-yl acetate and 14.4 g (0.1 mol) of 3-chloro-2-hydrazinopyridine were initially charged in 200 ml of ethanol, and the mixture was stirred at 25° c. for 3 h. The precipitate was filtered off and washed with cyclohexane.

This gave 34 g of the product (90% yield) as a white solid with a melting point of 105-106° C.

$^1$H NMR (DMSO $d_6$) δ: 2.07 (s, 3H), 3.30 (dt, 1H), 3.78 (dt, 1H), 4.79 (dt, 1H), 4.84 (dt, 1H), 7.23 (dd, 1H), 7.95 (dd, 1H), 8.22 (dd, 1H), 9.46 (br.s, 1H) ppm.

Example 5b

[1-(3-Chloropyridin-2-yl)-5-(trichloromethyl)-1H-pyrazol-3-yl]methanol 36.9 g of [1-(3-chloropyridin-2-yl)-5-(trichloromethyl)-1H-pyrazol-3-yl]methyl acetate were dissolved in 100 ml of ethanol, and 20 g of NaOH (as a 40% solution in water) were added. After 1 h, the mixture was diluted with 300 ml of water, and the product was filtered off, washed with water and dried. This gave 30 g (95%) of the product as a white solid.

M.p. 109-111° C.

$^1$H NMR (DMSO $d_6$) δ: 4.55 (2H); 6.95 (1H); 7.55 (dd, 1H); 8.05 (dd, 1H); 8.5 (dd, 1H) ppm.

Example 6

Hydrochloride of 1-(3-chloropyridin-2-yl)-3-(hydroxymethyl)-1H-pyrazole-5-carboxylic acid 38.7 g (0.1 mol) of [1-(3-chloropyridin-2-yl)-5-(trichloromethyl)-1H-pyrazol-3-yl]methanol and 10 g of $H_2SO_4$ (as a 10% solution in water) were stirred at 80° C. for 3 h.

The mixture was cooled to 0° C.; the precipitate was filtered off and washed with acetonitrile and dried.

Yield 90%, m.p. 173-175° C.

$^1$H NMR (DMSO $d_6$) δ: 3.5 (b.s, 1H) 4.50, (2H); 5.2 (b.s), 6.95 (1H); 7.55 (dd, 1H); 8.05 (dd, 1H); 8.5 (dd, 1H), 13 (b.s) ppm.

Example 7

2-[5-Carboxy-3-(hydroxymethyl)-1H-pyrazol-1-yl]-3-chloropyridinium hydrochloride The procedure is as described in Example 6, except using [1-(3-chloropyridin-2-yl)-5-(trichloromethyl)-1H-pyrazol-3-yl]methyl acetate Yield 95%, m.p. 173-175° C.

Example 8

3-[(Benzyloxy)methyl]-1-(3-chloropyridin-2-yl)-1H-pyrazole-5-carboxylic acid 4.4 g of 2-{3-[(benzyloxy)methyl]-5-(trichloromethyl)-1H-pyrazol-1-yl}-3-chloropyridine and 30 ml of 20% $H_2SO_4$ were heated at 100° C. for 24 h.

The precipitate was filtered off and washed with water. The yield was 92%.

Characterization:

$^1$H NMR (CDCl$_3$) δ: 4.61 (2H, s); 4.63 (m, 2H), 6.97 (1H, s); 7.2-7.4 (5H, m); 7.42 (1H, m); 7.96 (1H, d, 2 Hz); 8.5 (1H, d, 2 Hz) ppm.

Example 9

1-(3-Chloropyridin-2-yl)-3-(hydroxymethyl)-1H-pyrazole-5-carboxylic acid hydrochloride 3.43 g of 3-[(benzyloxy)methyl]-1-(3-chloropyridin-2-yl)-1H-pyrazole-5-carboxylic acid and 20 ml of HCl (37.5%) were heated at 100° C. for 2 h and then the reaction mixture was concentrated completely under reduced pressure at 10 mbar. This gave 1-(3-chloropyridin-2-yl)-3-(hydroxymethyl)-1H-pyrazole-5-carboxylic acid as the hydrochloride. Neutralization with NaHCO$_3$ afforded the free acid as a white solid. The yield was 94%.

Example 10

Methyl 3-(chloromethyl)-1-(3-chloropyridin-2-yl)-1H-pyrazole-5-carboxylate 1-(3-chloropyridin-2-yl)-3-(hydroxymethyl)-1H-pyrazole-5-carboxylic acid hydrochloride (0.1 mol) was initially charged in 100 ml of toluene. 24 g of SOCl$_2$ were added in portions at 60° C. The mixture was heated at 70° C. for 3 h, in the course of which the precipitate went completely into the solution. Methanol (30 ml) was slowly added dropwise to the mixture and the solution was stirred at 30° C. for a further 1 h.

Subsequently, the solution was concentrated under reduced pressure. This gave 95% of the product with a purity of 96%.

Characterization $^1$H NMR (CDCl$_3$) δ: 3.7 (3H, s); 4.7 (2H, s); 7.1 (1H, s); 7.5 (1H, m); 8.05 (1H, m); 8.5 (1H, m) ppm.

Example 11

Methyl 1-(3-chloropyridin-2-yl)-3-(hydroxymethyl)-1H-pyrazole-5-carboxylate 32.6 g of [1-(3-chloropyridin-2-yl)-5-(trichloromethyl)-1H-pyrazol-3-yl]methanol and 300 ml of methanol were heated in an autoclave at 90° C. for 3 h. Methanol was removed under reduced pressure and the precipitate was washed with water. Yield 25 g, 94%, m.p. 104° C.

Example 12

Methyl 3-(chloromethyl)-1-(3-chloropyridin-2-yl)-1H-pyrazole-5-carboxylate

Methyl 1-(3-chloropyridin-2-yl)-3-(hydroxymethyl)-1H-pyrazole-5-carboxylate (26.7 g, 0.1 mol) was dissolved in 150 ml of CH$_2$Cl$_2$ and the solution was cooled to 5° C. SOCl$_2$ (0.12 mol) in 30 ml of CH$_2$Cl$_2$ was slowly added dropwise at this temperature. The mixture was stirred at 40° C. for a further 4 h and concentrated under reduced pressure. The product can be used further without purification.

Analytical Characterization $^1$H NMR (CD$_3$CN) δ: 8.52 (1H, d); 8.06 (1H, d), 7.55 (1H, dd); 7.10 (1H, s); 4.75 (2H, s); 3.75 (3H, s) ppm.

The invention claimed is:

1. A process for preparing a compound of formula (I),

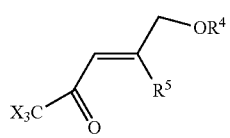
(I)

in which
R$^4$ is hydrogen, —(C═O)alkyl, (C═O)haloalkyl, —(C═O)O-alkyl, SO$_2$alkyl, SO$_2$-haloalkyl, SO$_2$-aryl,
X is halogen,
R$^5$ is alkoxy, dialkylamino where the alkyl groups may optionally form a ring which may optionally contain 1-2 further heteroatoms from the group of O, N, S, or is cycloalkylamino, thioalkyl,
said process comprising reacting a compound of formula (III)

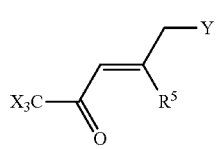
(III)

in which R$^5$ is as defined above and X and Y are independently fluorine, chlorine, bromine or iodine, with a compound of formula (II)

KatOR$^4$ (II)

in which
Kat is a cation, and is Li, Na, K, Cs, (alkyl)$_4$N, (alkyl)$_4$P, (aryl)$_4$P,
R$^4$ is hydrogen, —(C═O)alkyl, (C═O)haloalkyl, —(C═O)O-alkyl, SO$_2$alkyl, SO$_2$-haloalkyl, SO$_2$-aryl.

2. A compound of formula (I)

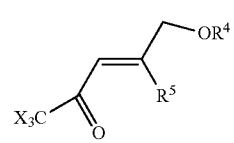
(I)

wherein
R$^4$ is hydrogen, —(C═O)alkyl, (C═O)haloalkyl, —(C═O)O-alkyl, SO$_2$alkyl, SO$_2$-haloalkyl, SO$_2$-aryl,
X is halogen, and
R$^5$ is alkoxy, dialkylamino, where the alkyl groups may optionally form a ring which may optionally contain 1-2 further heteroatoms from the group of O, N, S or is cycloalkylamino, or is thioalkyl.

3. A compound of formula (I) according to claim 2, wherein
R$^4$ is —(C═O)(C$_1$-C$_6$)alkyl, (C═O)halo(C$_1$-C$_6$)alkyl, —(C═O)O—(C$_1$-C$_6$)alkyl, SO$_2$(C$_1$-C$_6$)alkyl, SO$_2$-halo(C$_1$-C$_6$)alkyl, SO$_2$-aryl,
X is fluorine, chlorine or bromine, and
R$^5$ is alkoxy.

4. A compound of formula (I) according to claim 3, wherein
R$^4$ is —(C═O)(C$_1$-C$_6$)alkyl,
X is chlorine or bromine, and
R$^5$ is (C$_1$-C$_6$)alkoxy.

5. The process according to claim 1 wherein the reaction is effected in the presence of an acid.

6. The process according to claim 5 wherein the acid is selected from the group consisting of HCl, H$_2$SO$_4$, CH$_3$COOH and CF$_3$COOH.

7. The process according to claim 1 wherein the reaction is effected in the presence of a catalyst.

8. The process according to claim 6 wherein the acid is CH$_3$COOH.

9. The process according to claim 7 wherein the catalyst is tetrabutylammonium bromide.

10. The process according to claim 1 wherein the reaction is effected in the presence of an acid wherein said acid is selected from the group consisting of HCl, H2SO4, CH3COOH and CF3COOH.

* * * * *